US008788058B2

(12) United States Patent
Li et al.

(10) Patent No.: US 8,788,058 B2
(45) Date of Patent: *Jul. 22, 2014

(54) LEADS WITH HIGH SURFACE RESISTANCE

(71) Applicant: Cardiac Pacemakers, Inc., St. Paul, MN (US)

(72) Inventors: Yingbo Li, Woodbury, MN (US); Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,678

(22) Filed: Sep. 16, 2013

(65) Prior Publication Data

US 2014/0018896 A1   Jan. 16, 2014

Related U.S. Application Data

(63) Continuation of application No. 13/592,588, filed on Aug. 23, 2012, now Pat. No. 8,538,551, which is a continuation of application No. 12/329,257, filed on Dec. 5, 2008, now Pat. No. 8,275,464.

(60) Provisional application No. 60/992,915, filed on Dec. 6, 2007.

(51) Int. Cl.
 *A61N 1/05* (2006.01)
 *A61N 1/08* (2006.01)
 *A61N 1/37* (2006.01)

(52) U.S. Cl.
 CPC ............... *A61N 1/05* (2013.01); *A61N 1/3718* (2013.01); *A61N 1/056* (2013.01); *A61N 2001/086* (2013.01)
 USPC .................. 607/63; 607/115; 607/116

(58) Field of Classification Search
 USPC .................. 607/2, 63, 115–116
 See application file for complete search history.

(56) References Cited

U.S. PATENT DOCUMENTS

| 4,131,759 A | 12/1978 | Felkel |
| 4,484,586 A | 11/1984 | McMickle et al. |
| 5,554,139 A | 9/1996 | Okajima |
| 5,800,496 A | 9/1998 | Swoyer et al. |

(Continued)

FOREIGN PATENT DOCUMENTS

| EP | 0092798 A1 | 11/1983 |
| JP | 58192205 A | 11/1983 |

(Continued)

OTHER PUBLICATIONS

International Search Report and Written Opinion issued in PCT/US2008/085518 on Oct. 29, 2009, 15 pages.

(Continued)

*Primary Examiner* — Carl H Layno
*Assistant Examiner* — Jon Eric C Morales
(74) *Attorney, Agent, or Firm* — Faegre Baker Daniels LLP

(57) ABSTRACT

Implantable medical leads having resistance characteristics adapted to dissipate radio frequency (RF) electromagnetic energy during medical procedures such as magnetic resonance imaging (MRI) are disclosed. An illustrative medical device includes a lead having an inner electrical conductor operatively coupled to an electrode and a pulse generator, and one or more outer resistive shields that radially surround the inner conductor and dissipate RF energy into the surrounding body tissue along the length of the lead.

20 Claims, 13 Drawing Sheets

(56) References Cited

U.S. PATENT DOCUMENTS

| | | |
|---|---|---|
| 5,954,760 A | 9/1999 | Jarl |
| 6,143,013 A | 11/2000 | Samson et al. |
| 6,671,554 B2 | 12/2003 | Gibson et al. |
| 6,876,886 B1 | 4/2005 | Wang |
| 6,980,865 B1 | 12/2005 | Wang et al. |
| 7,013,180 B2 | 3/2006 | Dublin et al. |
| 7,015,392 B1 | 3/2006 | Dickenson |
| 7,123,013 B2 | 10/2006 | Gray |
| 7,138,582 B2 | 11/2006 | Lessar et al. |
| 7,174,219 B2 | 2/2007 | Wahlstrand et al. |
| 7,174,220 B1 | 2/2007 | Chitre et al. |
| 7,388,378 B2 | 6/2008 | Gray et al. |
| 7,410,485 B1 | 8/2008 | Fink et al. |
| 7,551,966 B2 | 6/2009 | MacDonald |
| 8,244,346 B2 | 8/2012 | Foster et al. |
| 8,275,464 B2 * | 9/2012 | Li et al. ............ 607/63 |
| 8,538,551 B2 * | 9/2013 | Li et al. ............ 607/63 |
| 2003/0014080 A1 | 1/2003 | Baudino |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144705 A1 | 7/2003 | Funke |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0162600 A1 | 8/2004 | Williams |
| 2004/0210289 A1 | 10/2004 | Wang et al. |
| 2005/0065587 A1 | 3/2005 | Gryzwa |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0283167 A1 | 12/2005 | Gray |
| 2006/0030774 A1 | 2/2006 | Gray et al. |
| 2006/0041294 A1 | 2/2006 | Gray |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2007/0106332 A1 | 5/2007 | Denker et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2008/0033497 A1 | 2/2008 | Bulkes et al. |
| 2008/0132985 A1 | 6/2008 | Wedan et al. |
| 2008/0195186 A1 | 8/2008 | Li et al. |
| 2008/0262584 A1 | 10/2008 | Bottomley et al. |
| 2009/0149920 A1 | 6/2009 | Li et al. |
| 2009/0149934 A1 | 6/2009 | Ameri et al. |
| 2009/0171421 A1 | 7/2009 | Atalar et al. |
| 2010/0036466 A1 | 2/2010 | Min et al. |
| 2012/0130453 A1 | 5/2012 | Stahmann et al. |
| 2012/0323297 A1 | 12/2012 | Li et al. |

FOREIGN PATENT DOCUMENTS

| | | | |
|---|---|---|---|
| JP | 8308934 A | | 11/1996 |
| JP | 2003047653 A | | 2/2003 |
| JP | 2004141679 A | | 5/2004 |
| JP | 2005515854 A | | 6/2005 |
| WO | WO2005081784 A2 | | 9/2005 |
| WO | WO2007047966 A2 | | 4/2007 |

OTHER PUBLICATIONS

International Search Report and Written Opinion issued in PCT/US2008/085533, mailed Aug. 26, 2010.

International Search Report and Written Opinion issued in PCT/US2008/087068 on Aug. 3, 2009.

International Search Report and Written Opinion issued in PCT/US2011/052684, mailed Jan. 25, 2012, 11 pages.

Invitation to Pay Additional Fees and Partial Search Report, dated Aug. 17, 2009, issued in PCT/US2008/085533, 6 pages.

* cited by examiner

LEADS WITH HIGH SURFACE RESISTANCE

CROSS-REFERENCE TO RELATED APPLICATION

This application is a continuation of U.S. application Ser. No. 13/592,588, filed on Aug. 23, 2012, now U.S. Pat. No. 8,538,551, which is a continuation of U.S. application Ser. No. 12/329,257, filed on Dec. 5, 2008, now U.S. Pat. No. 8,275,464, which claims priority under 35 U.S.C. §119 to U.S. Provisional Application No. 60/992,915, filed on Dec. 6, 2007, entitled "Leads With High Resistive Surface," to each of which the benefit of priority is claimed and all of which are incorporated herein by reference in their respective entireties.

TECHNICAL FIELD

The present invention relates to implantable medical devices. More specifically, the present invention relates to implantable medical leads having impedance characteristics adapted to dissipate radio frequency (RF) electromagnetic energy during medical procedures such as magnetic resonance imaging (MRI).

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a static magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the shape and surface area of the lead electrodes. In some cases, exposure to electromagnetic energy may also induce an undesired voltage on the lead.

SUMMARY

The present invention relates to implantable medical leads having impedance characteristics adapted to dissipate RF electromagnetic energy during medical procedures such as magnetic resonance imaging (MRI). An illustrative implantable medical device (IMD) configured for use in a magnetic resonance imaging environment includes a lead having an inner electrical conductor operatively coupled to an electrode, and at least one resistive shield that radially surrounds the inner electrical conductor along all or a portion of the length of the lead. The inner electrical conductor can comprise a material having a relatively low resistance to facilitate energy transmission of IMD electrical signals through the conductor to the lead electrode. The inner conductor may have a relatively low impedance at the IMD such that it does not attenuate electrical energy transmitted by the IMD (e.g., electrical pulses transmitted by a pulse generator).

The outer resistive shield has a resistance that is relatively large in comparison to the resistance of the inner conductor, which dissipates RF electromagnetic energy received on the lead during an MRI scan along the length of the lead. In some embodiments, the outer resistive shield includes a layer or coating of resistive material radially disposed about at least a portion of the inner conductor. In other embodiments, the outer resistive shield includes a helically-shaped coil radially disposed about at least a portion of the inner conductor. The resistive shield can comprise a single resistive shield that extends continuously along the length of the lead, or can comprise multiple resistive shields each spaced apart from each other along the length of the lead via a gap, which serves to electrically isolate the resistive shields from each other. In use, the resistive shields minimize the energy pickup by the inner portion of the lead, and the high impedance of the shields at the frequency of the MRI RF energy minimizes the transfer of any energy picked up by the lead to the lead electrode.

A medical device in accordance with another illustrative embodiment includes a lead having an electrical conductor wire operatively coupled to an electrode. The conductor wire can vary in resistivity either continuously or at one or more locations across the width of the lead such that an outer portion of the conductor has a greater resistivity than the resistivity at a center portion of the conductor. In some embodiments, for example, the conductor wire includes an inner conductor core surrounded radially by one or more outer resistive shields configured to dissipate RF electromagnetic energy along the length of the lead. In other embodiments, the resistivity of the conductor wire varies continuously across its width between the center portion and the outer portion.

Figure 1:
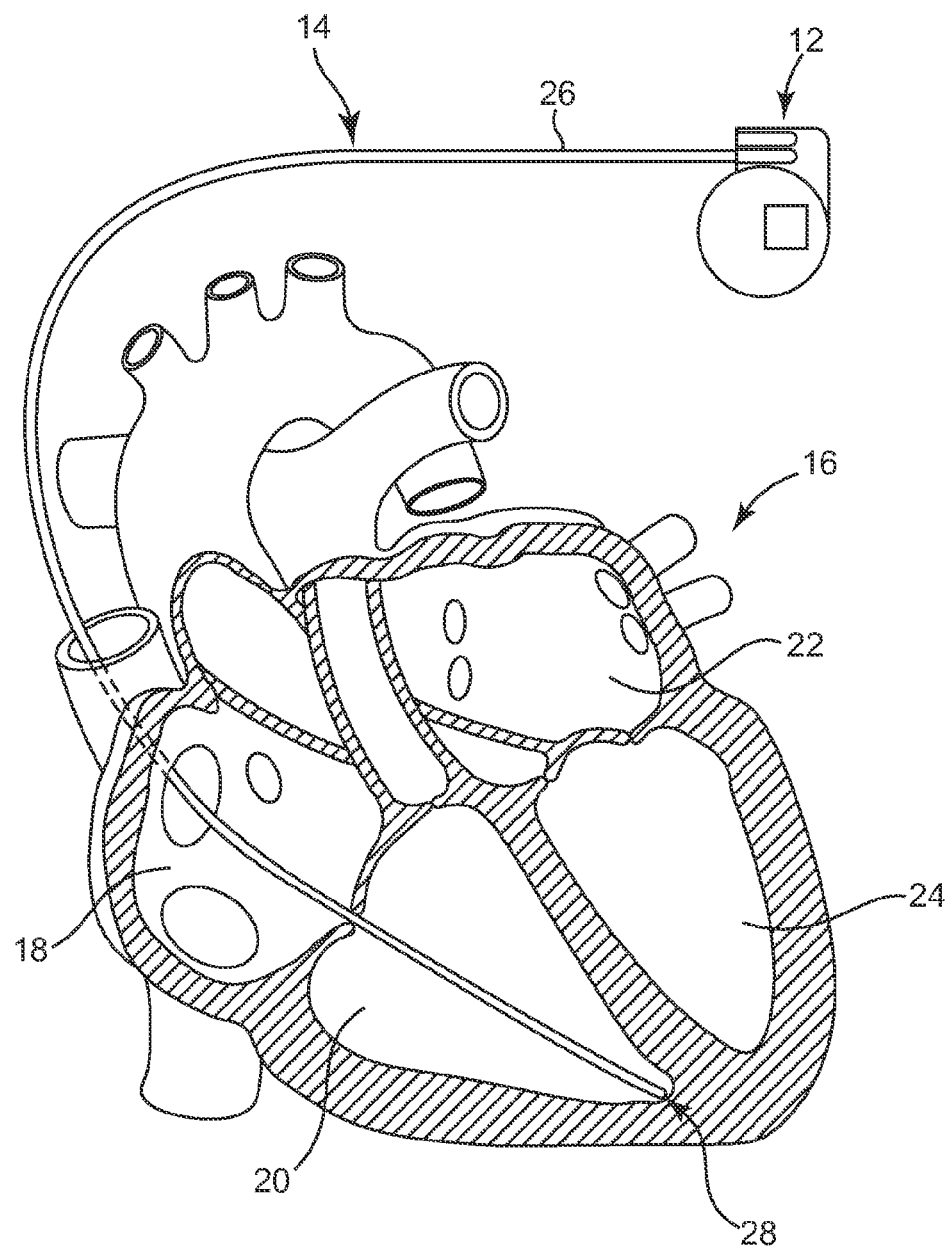
FIG. 1 is a schematic view of an illustrative medical device having a lead implanted within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative medical device 12 having a lead implanted within the body of a patient. In the illustrative embodiment depicted, the medical device 12 comprises a pulse generator implanted within the body. The medical device 12 can be coupled to a lead 14 inserted into the patient's heart 16. The heart 16 includes a right atrium 18, a right ventricle 20, a left atrium 22, and a left ventricle 24. The pulse generator 12 can be implanted subcutaneously within the body, typically at a location such as in the patient's chest or abdomen, although other implantation locations are possible.

A proximal portion 26 of the lead 14 can be coupled to or formed integrally with the pulse generator 12. A distal portion 28 of the lead 14, in turn, can be implanted at a desired location within the heart 16 such as in the right ventricle 20, as shown. Although the illustrative embodiment depicts only a single lead 14 inserted into the patient's heart 16, in other embodiments, however, multiple leads can be utilized so as to electrically stimulate other areas of the heart. 16. In some embodiments, for example, the distal portion of a second lead (not shown) may be implanted in the right atrium 18. In addition, or in lieu, another lead may be implanted at the left side of the heart 16 (e.g., in the coronary veins) to stimulate the left side of the heart 16. Other types of leads such as epicardial leads may also be utilized in addition to, or in lieu of, the lead 14 depicted in FIG. 1.

During operation, the lead 14 can be configured to convey electrical signals between the heart 16 and the pulse generator 12. For example, in those embodiments where the pulse generator 12 is a pacemaker, the lead 14 can be utilized to deliver electrical therapeutic stimulus for pacing the heart 16. In those embodiments where the pulse generator 12 is an implantable cardiac defibrillator, the lead 14 can be utilized to deliver electric shocks to the heart 16 in response to an event such as a heart attack. In some embodiments, the pulse generator 12 includes both pacing and defibrillation capabilities.

Figure 2:
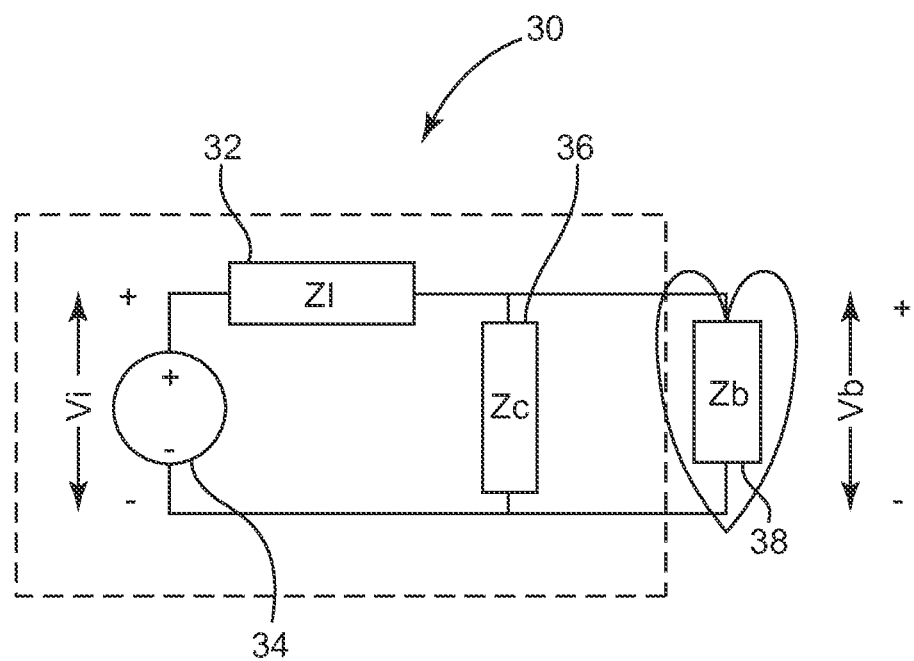
FIG. 2 is a schematic view showing a simplified equivalence circuit for the lead of FIG. 1.

FIG. 2 is a schematic view showing a simplified equivalence circuit 30 for the lead 14 representing the RF energy picked up on the lead 14 resulting from RF electromagnetic energy produced by an MRI scanner. As shown in FIG. 2, Vi 34 in the circuit 30 represents an equivalent source of energy picked up by the lead 14 from the MRI scanner.

During magnetic resonance imaging, the length of the lead 14 functions similar to an antenna, receiving the RF energy that is transmitted into the body from the MRI scanner. Voltage 34 in FIG. 2 may represent, for example, the resultant voltage received by the lead 14 from the RF energy. The RF energy picked-up by the lead 14 may result, for example, from the rotating RF magnetic field produced by an MRI scanner, which generates an electric field in the plane perpendicular to the rotating magnetic field vector in conductive tissues. The tangential components of these electric fields along the length of the lead 14 couple to the lead 14. The voltage Vi 34 is thus equal to the integration of the tangential electric field (i.e., the line integral of the electric field) along the length of the lead 14.

The ZI parameter 32 in the circuit 30 represents the equivalent impedance exhibited by the lead 14 at the RF frequency of the MRI scanner. The impedance value ZI 32 may represent, for example, the inductance or the equivalent impedance resulting from the parallel inductance and the coil turn by turn capacitance exhibited by the lead 14 at an RF frequency of 64 MHz for a 1.5 Tesla MRI scanner, or at an RF frequency of 128 MHz for a 3 Tesla MRI scanner. The impedance ZI of the lead 14 is a complex quantity having a real part (i.e., resistance) and an imaginary part (i.e., reactance).

Zb 38 in the circuit 30 may represent the impedance of the body tissue at the point of lead contact. Zc 36, in turn, may represent the capacitive coupling of the lead 14 to surrounding tissue along the length of the lead 14, which may provide a path for the high frequency current (energy) to leak into the surrounding tissue at the RF frequency of the MRI scanner. Minimizing the absorbed energy (represented by source Vi 34) reduces the energy that is transferred to the body tissue at the point of lead contact with the tissue.

The circuit represented in FIG. 2 and the associated equation described below are for the purpose of illustrating the concept of lead heating in an MRI environment. At frequencies where the wavelength of induced voltage (or current) is close to the size of the circuit, a simple lumped sum system such as that illustrated in FIG. 2 may not accurately model the behavior of the lead 14 in the MRI environment. Consequently, in those circumstances, a distributed model should be used along with Maxwell's equation for a proper mathematical description of the circuit. In some cases, the approximating distributed model can be created using field solvers or simulators.

As can be further seen in FIG. 2, the lead 14 has some amount of leakage 36 into the surrounding tissue at the RF frequency of the MRI scanner. As further indicated by 38, there is also an impedance at the point of contact of the lead electrode to the surrounding body tissue within the heart 16. The resulting voltage Vb delivered to the body tissue may be related by the following formula:

$$Vb = Vi\, Zbe/(Zbe - Zl),\ \text{where}\ Zbe = Zb\ \text{in parallel with}\ Zc.$$

The temperature at the tip of the lead 14 where contact is typically made to the surrounding tissue is related in part to the power dissipated at 38 (i.e., at "Zb"), which, in turn, is related to the square of Vb. To minimize temperature rises resulting from the power dissipated at 38, it is thus desirable to minimize Vi (34) and Zc (38) while also maximizing the impedance of the lead ZI (32). In some embodiments, the impedance ZI (32) of the lead 14 can be increased at the RF frequency of the MRI scanner, which aids in reducing the power dissipated into the surrounding body tissue at the point of contact 38.

In some embodiments, the impedance of the lead 14 can be increased by adding inductance to the lead 14 and/or by a suitable construction technique. For example, the inductance of the lead 14 can be increased by increasing the diameter of the conductor coil and/or by decreasing the pitch of the conductor coil. Decreasing the coil pitch may result in increasing capacitance between successive turns of the coil (i.e., coil turn by turn capacitance). The parallel combination of inductance (from the helical shape of the coil) and the turn by turn capacitance constitutes a resonance circuit. For a helically coiled lead construction, if the resonance frequency of the lead is above the RF frequency of the MRI, then the helical coil acts as an inductor. For an inductor, increasing the cross section of the coil area and/or reducing the coil pitch increases the inductance and, as a result, increases the impedance of the lead 14.

Similar to an antenna, the energy pickup from a lead is related to its resonance length with respect to the wavelength of the frequency of interest. For example, for a dipole antenna, the antenna is considered tuned, or at resonance, when the antenna length is half the wavelength or an integer multiple of the wavelength. At resonance lengths, the energy pickup of the antenna is maximized. In a similar manner, and in some embodiments, the lead 14 can be detuned so as to prevent resonance within the lead 14, and thus minimize the voltage Vi. For the illustrative embodiment shown in FIG. 1, for example, the lead 14 functions as an antenna having a resonance frequency at length $L = \text{integer} \times \lambda/2$. In some embodiments, the length of the lead 14 and/or the construction parameters of the lead 14 affecting the wavelength can be chosen so as to avoid resonance within the lead 14.

In some embodiments, in addition to detuning the length of the lead 14 with respect to the wavelength of the MRI induced RF energy, shielding can also be added to the lead 14 to further reduce the amount of electromagnetic energy picked-up from the lead 14. For example, the energy picked up from the shielding can be coupled to the patient's body along the length of the lead 14, preventing the energy from coupling to the lead tip. The transfer of intercepted energy by the shielding along the length of the shielding/lead can also be inhibited by dissipating the energy as resistive loss, using resistive material for the shielding construction.

Figure 3:
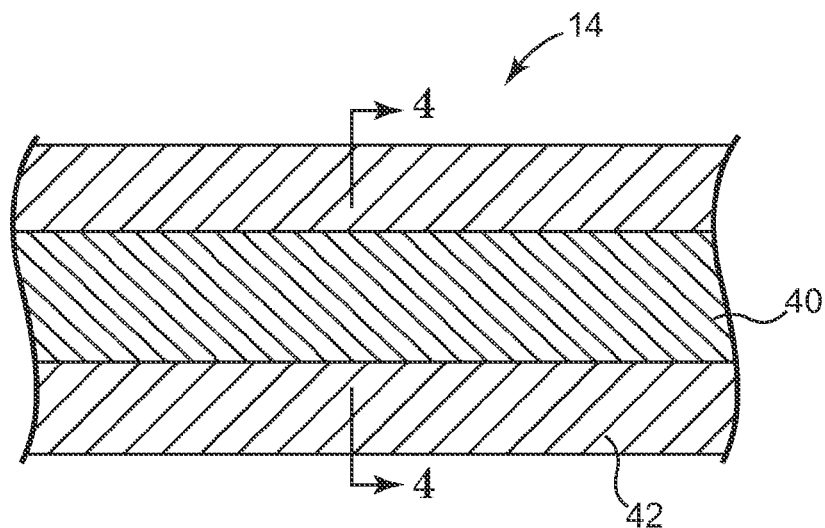
FIG. 3 is a longitudinal cross-sectional view showing a portion of the lead of FIG. 1 in greater detail.
Figure 4:
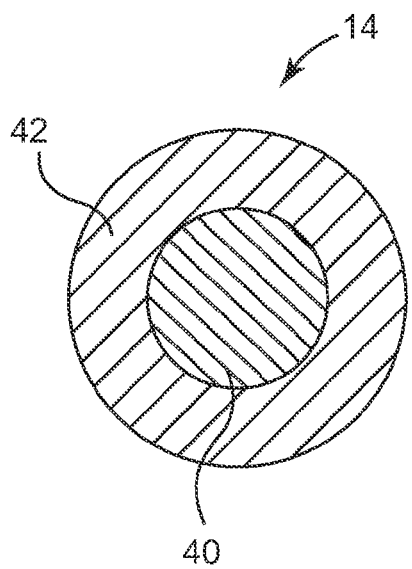
FIG. 4 is a transverse cross-sectional view showing the lead across line 4-4 in FIG. 3.

FIG. 3 is a longitudinal cross-sectional view showing a portion of the lead 14 of FIG. 1 in greater detail. FIG. 4, in turn, is a transverse cross-sectional view showing the lead 14 across line 4-4 in FIG. 3. As shown in FIGS. 3-4, the lead 14 includes an inner conductor core 40 and an outer resistive shield 42 that radially surrounds the inner conductor 40 along at least a portion of the length of the lead 14. The inner conductor core 40 may function as an electrical conduit for supplying energy from the pulse generator 12 to one or more electrodes (not shown) located on the distal portion 28 of the lead 14. In those embodiments where the lead 14 is a bradycardia lead, for example, the inner conductor core 40 may serve as an electrical conduit for supplying therapeutic energy to one or more electrodes used for pacing the patient's heart 16 and/or for sensing electrical activity occurring within the heart 16. Alternatively, in those embodiments where the lead 14 is a tachycardia lead, the inner conductor core 40 may serve as an electrical conduit for supplying shocking energy to one or more electrodes coils located on the distal portion 28 of the lead 14. Although a single inner conductor core 40 is shown in the embodiment of FIGS. 3-4, in other embodiments multiple inner conductors may be provided for transmitting electrical energy to multiple pacing/sense electrodes located on the lead 14.

In the illustrative embodiment of FIGS. 3-4, the lead 14 has a substantially coaxial configuration with the inner conductor core 40 extending co-linearly with the outer resistive shield 42 along all or a portion of the length of the lead 14. In other embodiments, the inner conductor core 40 can comprise a helically-shaped conductor coil (or multiple co-radially wound helically-shaped conductors) extending through the interior of the outer resistive shield 42 along all or a portion of the length of the lead 14.

The outer resistive shield 42 can comprise a layer or coating of resistive material that radially surrounds the inner conductor core 40. In one embodiment, for example, the outer resistive shield 42 comprises a resistive jacket that is formed integrally with the inner conductor 40 (e.g., as a single conductor) that radially surrounds the inner conductor core 40. In some embodiments, the lead 14 may further include a layer or coating of insulative material about the resistive shield 42 to electrically isolate the conductor core 40 from the surrounding body tissue and blood. In further embodiments discussed herein in which there is a layer or coating of insulation between the conductor and the resistive shield, the layer or coating of insulative material disposed about the resistive shield 42 may be omitted, provided the length of the conductor is sufficiently small.

The outer resistive shield 42 may have a relatively high resistance in comparison to the inner conductor core 40 in order to facilitate dissipation of RF electromagnetic energy received along the length the lead 14, which can cause heating of body tissue in contact with the lead 14. In some embodiments, for example, the ratio of the resistance of the outer resistive shield 42 to the resistance of the inner conductor core 40 may be in the range of between about 2 to 10. An example resistance of the outer resistive shield 42 may be approximately 1 kΩ for a 50 cm long length of lead, although other values are possible.

In some embodiments, the difference in the resistance between the outer resistive shield 42 and the inner conductor core 40 can depend at least in part on the type of material(s) used, the dielectric constant of those materials, as well as other factors. In certain embodiments, for example, the inner conductor core 40 comprises a relative low resistance material configured to facilitate low-energy transmission of electrical signals along the core 40 whereas the outer resistive shield 42 comprises a relatively high resistance material configured to dissipate RF electromagnetic energy received on the lead 14 along the length of the lead 14 during magnetic resonance imaging. High resistance materials suitable for use as an outer resistive shield 42 can include, for example, metals, conductive polymers, and/or composite materials. In one exemplary embodiment, the inner conductor core 40 is a silver-filled MP35N wire containing approximately 28% to 30% silver whereas the outer resistive shield 42 comprises a layer or coating (e.g., a tubular jacket) of a different, more resistive material. An example conductive polymer suitable for use as the outer resistive shield 42 is polyphenylenevinylene or polyfluorene.

Although a higher conductivity shield generally provides better shielding of the inner conductor, and also permits thinner shielding to be used due to the lower skin depth, the higher conductivity of such shielding may also transfer the RF energy more easily along the length of the lead. Thus, even though the RF energy does not couple from the shield to the inner conductor, the shield itself may transfer the RF energy along the length of the lead towards the electrode at the lead tip. At or near the electrode, this high concentration of energy either directly heats the surrounding tissue (e.g., by capacitively coupling to the tissue), or couples the energy back to the lead where the inner conductor is exposed and contacts the tissue.

Figure 5:
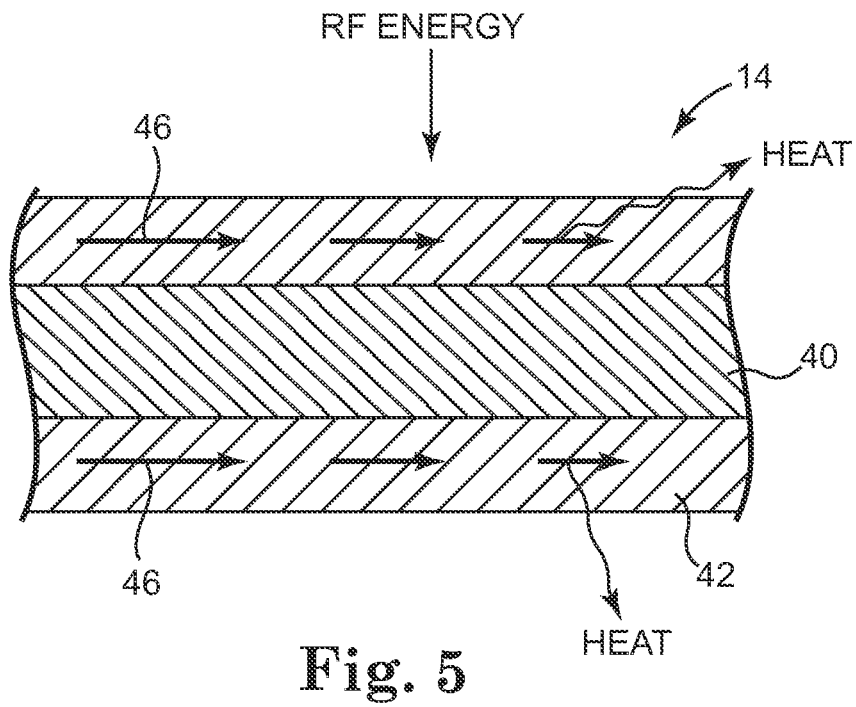
FIGS. 5 and 6 are longitudinal and transverse cross-sectional views, respectively, showing the energy flow path of RF electromagnetic energy received on the lead of FIGS. 3-4 in the presence of an MRI field.
Figure 6:
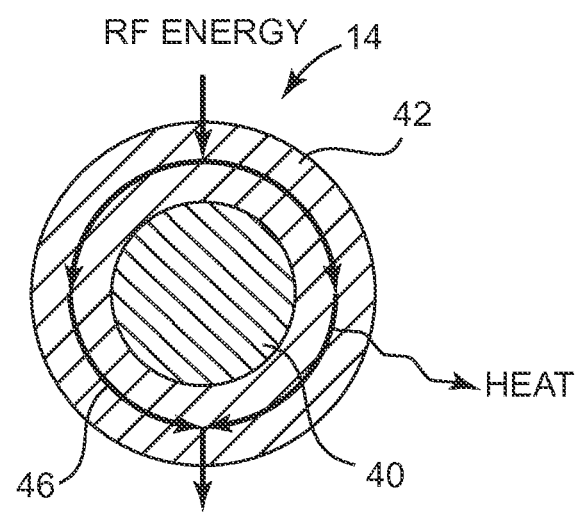

FIGS. 5 and 6 are longitudinal and transverse cross-sectional views, respectively, showing the energy flow path of RF electromagnetic energy received on the lead 14 of FIGS. 3-4 in the presence of an MRI field. As shown in FIGS. 5 and 6, RF energy transmitted into the patient's body during magnetic resonance imaging is received along the length of the lead 14, which acts as an antenna. Due to the "skin effect" property in conductive wires, in which alternating currents are limited to conduction at or near the surface of a conductor, the resistance increases towards the center of the lead. The increase of the resistance of the shield toward the center may also be enhanced by providing insulating material about the shielding in some embodiments. As energy travels along the length of the lead 14, as indicated generally by reference arrows 46, the magnitude of the energy is reduced (due to dissipation), and the dissipated energy is converted to heat along the length of the lead 14. This can be seen generally by the reduction in the vector length of the arrows 46 from left to right in FIG. 5. As can be further seen in FIG. 6, the energy 46 takes the lowest impedance path of the resistive shield 42 instead of coupling to the inner conductor 40 due to the skin effect. Because the RF energy is dissipated along the length of the lead 14 and not at the electrode/body tissue interface, the heat absorbed by the lead from the RF energy is attenuated along the length of the lead 14.

Figure 7:
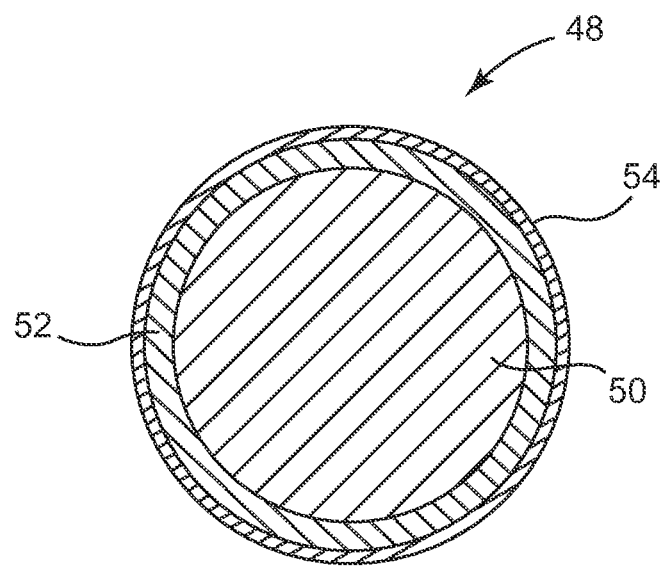
FIG. 7 is a transverse cross-sectional view showing a lead in accordance with another illustrative embodiment having a low thermal impedance insulator radially disposed about the resistive shield.

FIG. 7 is a transverse cross-sectional view showing a lead 48 in accordance with another illustrative embodiment having a low-thermal impedance insulator radially disposed about the resistive shield. The lead 48 is similar to the lead 14 described with respect to FIGS. 3-4, including an inner conductor core 50 that can be used as an electrical conduit for supplying energy to one or more electrodes on the lead 48, and an outer resistive shield 52 having a relatively high resistance compared to the resistance of the inner conductive core 50 for dissipating RF electromagnetic energy along the length of the lead 48.

In the embodiment of FIG. 7, the lead 48 further includes a low thermal impedance insulator 54 adapted to transfer heat generated along the length of the lead 48 at the lead/tissue interface. In some embodiments, the insulator 54 comprises a layer or coating of an insulative material radially disposed about the outer resistive shield 52. In certain embodiments, for example, the insulator 54 is a thin layer or coating of silicone or polyurethane, although other configurations are possible. In other embodiments, the insulator 54 is a thin layer or coating of metal radially disposed about the outer resistive shield 52. In some embodiments, the thickness of the metal insulator 54 is within the range of between about 10 µm to about 10,000 µm, although other configurations are possible.

In some embodiments, the material used for the insulator 54 has a relatively high dielectric constant in the range of between about 6 to 100. In some embodiments, the relatively high dielectric constant for the insulator material can be achieved by adding carbon particles, boron nitride particles, aluminum oxide particles, or the like to the insulator material. The insulator 54 can have a gradient of the dielectric constant that is constant along the length of the lead 48, constant across the width (or transverse cross section) of the lead 48, or a combination of both. During magnetic resonance imaging, the properties of the insulator 54, including its thickness, dielectric constant, or a combination of both, can provide a means for transferring electromagnetic energy and/or the heat generated by the resistive shield 52 to the surrounding body tissue along the length of the lead 48.

Figure 8:
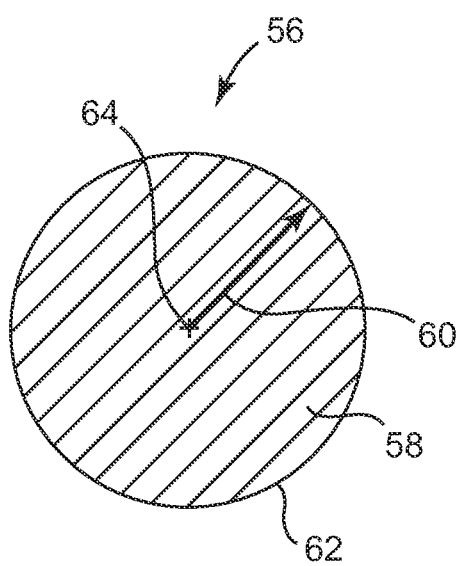
FIG. 8 is a traverse cross-sectional view showing a lead in accordance with another illustrative embodiment having a gradual change in resistance across its width.

FIG. 8 is a transverse cross-sectional view showing a lead 56 in accordance with another illustrative embodiment having a gradual change in resistivity across its width. In the embodiment of FIG. 8, the lead 56 includes a single conductor 58 having a variable resistivity across its width. As indicated generally by reference arrow 60, for example, the resistivity of the conductor 58 can vary across its width such that the resistivity is greatest at the outer surface 62 of the lead 56 where the lead 56 contacts the surrounding body tissue. In some embodiments, the resistivity of the lead 56 continuously increases from a center portion 64 of the conductor 58 to the outer surface 62. In other embodiments, the resistivity may increase at one or more finite locations across the width of the lead 56.

During an MRI scan, the increased resistivity towards the outer surface 62 of the lead 56 serves to dissipate the RF energy received from the MRI device at or near the outer surface 62 along the length of the lead 56, thus minimizing the amount of energy transmitted into the interior of the lead 56. This attenuation of the RF energy at or near the outer surface 62 prevents alternating currents from being transmitted through the interior conductor 58 to the electrodes located at the lead tip.

Figure 9:
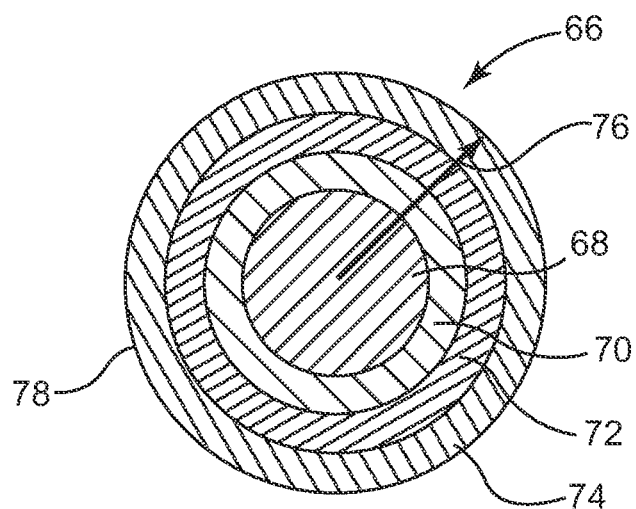
FIG. 9 is a transverse cross-sectional view showing a lead in accordance with another illustrative embodiment having multiple layers of conductors each with a different resistivity.

FIG. 9 is a transverse cross-sectional view showing a lead 66 in accordance with another illustrative embodiment having multiple layers of conductors each with a different resistivity. As shown in FIG. 9, the lead 66 includes an inner conductor 68 surrounding radially by a number of outer, relatively high resistance conductors 70,72,74. Each of the outer conductors 70,72,74 can have a different resistivity such that the resistance of the lead 66 varies across its width. In some embodiments, and as indicated generally by reference arrow 76, the resistivity of each of the outer conductor layers 70,72,74 may successively increase across the width of the lead 66 such that the resistivity is greatest at or near the outer surface 78 of the lead 66. In certain embodiments, for example, a first outer conductor layer 70 may have a first resistivity, a second outer conductor layer 72 may have a second resistivity greater than the first resistivity, and a third outer conductor layer 74 may have a third resistivity greater than the first and second resistivities. The number and arrangement of the conductor layers may differ, however. For example, while three outer conductor layers 70,72,74 are depicted in FIG. 9, in other embodiments a greater or lesser number of outer conductor layers each having a successively larger resistivity towards the outer surface 78 may be provided to dissipate RF energy received on the lead 66 during an MRI scan.

Although FIGS. 8 and 9 illustrate embodiments in which the lead resistivity varies either continuously or at one or more finite locations across the width of the lead 56,66, other embodiments in which the impedance varies along all or a portion of the length of the lead 56,66 are also possible. In some embodiments, for example, the impedance of the lead 56,66 increases along the length of the lead 56,66 such that the distal portion of the lead has a greater impedance than at the proximal portion of the lead. The change in impedance along the length of the lead can be achieved by the selection of materials having a particular characteristic (e.g., a high dielectric, resistivity, etc.), by the construction of the lead (e.g., inductance), by the dimensions of the lead (e.g., surface area of the lead), as well as other factors. Creating impedance discontinuities along the length of the lead by changing the impedance of the lead along the lead length has an effect on the energy pickup of the lead during an MRI scan. In some embodiments, these discontinuities can be distributed along the length of the lead so as to prevent a standing wave from being generated along the length of the lead, thus minimizing tissue heating at the lead electrode.

Figure 10:
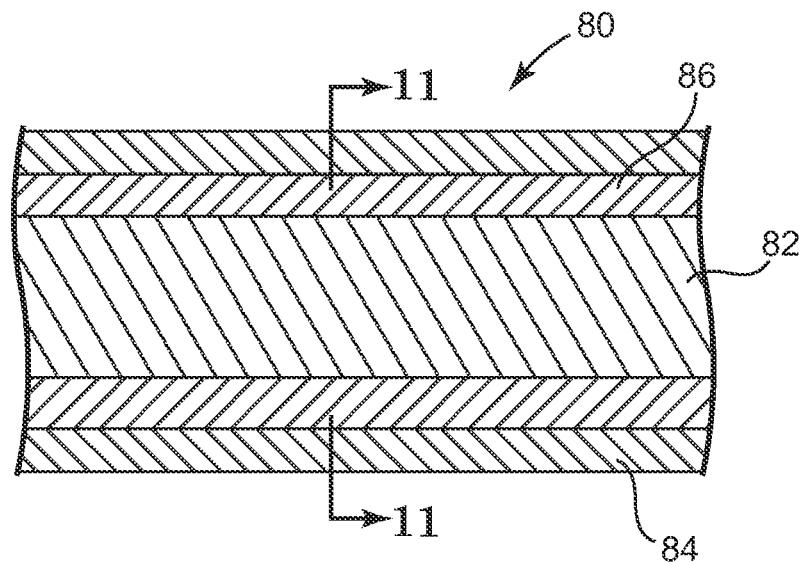
FIG. 10 is a longitudinal cross-sectional view showing a lead in accordance with another illustrative embodiment having an insulator between the resistive shield and the inner conductor.
Figure 11:
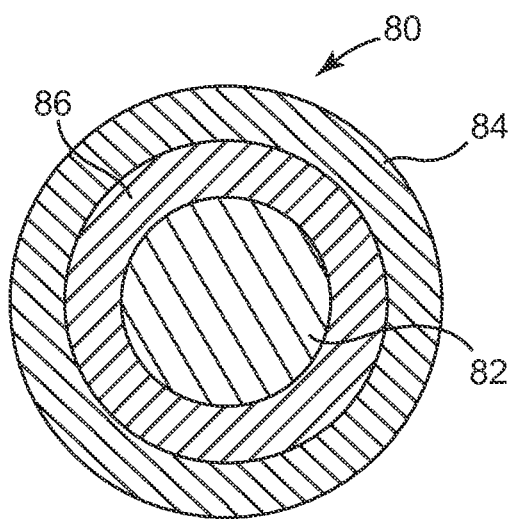
FIG. 11 is a transverse cross-sectional view showing the lead across line 11-11 in FIG. 10.

FIG. 10 is longitudinal cross-sectional view showing a lead 80 in accordance with another illustrative embodiment having an insulator between the resistive shield and the inner conductor. FIG. 11, in turn, is a transverse cross-sectional view showing the lead 80 across line 11-11 in FIG. 10. The lead 80 is similar to the lead 14 described with respect to FIGS. 3-4, including an inner conductor core 82 that can be used as an electrical conduit for supplying energy to one or more electrodes on the lead 80, and an outer resistive shield 84 having a relatively high resistance compared to the resistance of the inner conductor core 82 for dissipating RF energy along the length of the lead 80.

In the embodiment of FIGS. 10-11, the lead 80 further includes a layer of insulation 86 disposed between the outer resistive shield 84 and the inner conductor core 82. The layer of insulation 86 is configured to electrically isolate the inner conductor core 82 from RF energy received on the outer resistive shield 84. An example of a layer of insulation 86 suitable for electrically isolating the inner conductor core 80 is a thin layer less than or equal to about 10 mils. If another insulation layer or coating is placed about the resistive shield 84, then the layer of insulation 86 employed may be thinner, in some embodiments less than or equal to about 1 mil thickness. In certain embodiments, the outer diameter of the lead 80, including the inner coil conductor 82, the resistive shield 84, and the insulation 86 is about 50 to 100 mils.

In various embodiments, the resistive shielded wire can be wound to make a coiled conductor, which adds further impedance to the lead by increasing the inductance. In the embodiment of FIG. 3, for example, the conductor 40 and resistive shield 42 can be helically coiled, similar to the illustrative lead 118 discussed further herein, for example, with respect to FIG. 18, thus adding an inductance to the conductor 40. In some embodiments, the resistive shielded wire used for coil construction may be relatively thin (e.g., less than 10 mils). In some embodiments, the coiled conductor can be inserted into insulation tubing or sheathing (e.g., 10 mil insulative tubing) to prevent the coil conductor from contacting the tissue and blood at the implantation site. If each of the wires forming the conductor has a layer of insulation, then the insulation tubing or sheathing placed about the coil conductor is generally very thin (e.g., not more than about 1 mil).

Figure 12:
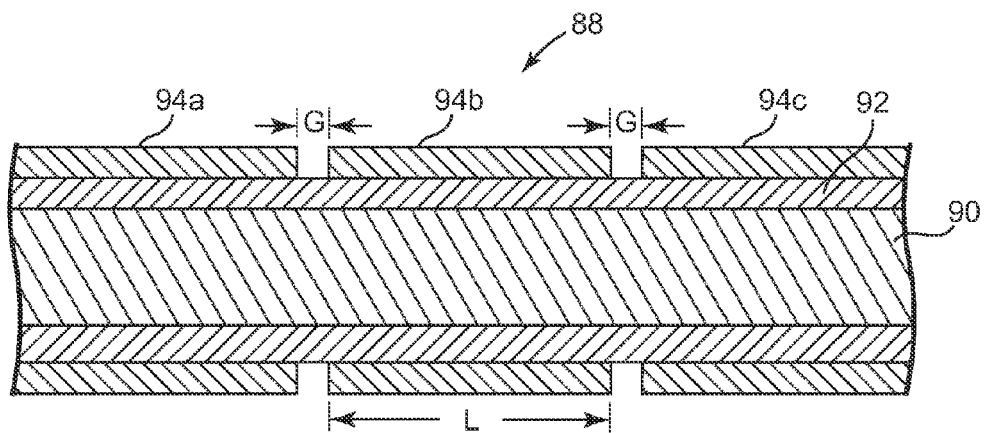
FIG. 12 is a longitudinal cross-sectional view showing a lead in accordance with another illustrative embodiment having a number of resistive shields spaced apart and electrically isolated from each other along the length of the lead.

FIG. 12 is a longitudinal cross-sectional view showing a lead 88 in accordance with another illustrative embodiment having a number of resistive shields spaced apart and electrically isolated from each other along the length of the lead. As shown in FIG. 12, the lead 88 is similar to that shown in FIG. 10, including an inner conductor core 90 that can be used as an electrical conduit for supplying energy to one or more electrodes on the lead 88, and a layer of insulation 92 radially surrounding the inner conductor core 90.

In the embodiment of FIG. 12, the lead 88 further includes a number of outer resistive shields 94a,94b,94c radially disposed about the layer of insulation 92 and the inner conductor core 90. Each of the outer resistive shields 94a,94b,94c can comprise a layer or coating of material having a resistance that is relatively large in comparison to the resistance of the inner conductor core 90. In some embodiments, for example, the ratio of the resistance of one of the outer resistive shields 94a,94b,94c to the inner conductor core 90 can be in the range of between about 2 to 10.

The outer resistive shields 94a,94b,94c each extend along a portion of the length of the lead 88, and are separated from each other via a number of small gaps G, as shown. The gap G between each longitudinally adjacent shield 94a,94b,9c can be sufficient such that each shield 94a,94b,94c is electrically isolated from the other shields 94a,94b,94c. In some embodiments, for example, the outer resistive shields 94a,94b,94c can be separated from each other by a gap G of approximately 4 mm to 5 mm. In other embodiments, the gap G separating each of the outer resistive shields 94a,94b,94c may be greater or lesser depending on the electrical characteristics of the shields 94a,94b,94c (e.g., the material and thickness of the shields 94a,94b,94c), the amount of RF energy received on the lead 88, as well as other factors.

The length L of each of the resistive shields 94a,94b,94c can be selected to detune sections of the shields 94a,94b,94c and prevent resonance based on the frequency of the RF energy provided by the MRI device. In some embodiments, for example, each of the outer resistive shields 94a,94b,94c has a length L that is less than or equal to ¼ of the wavelength of the RF energy received on the lead 88, thus detuning each of the shields 94a,94b,94c. In use, the picked up energy can be evenly distributed along the length of the lead (and dissipated evenly in the resistive material) instead of concentrating near the ends of each shield 94a,94b,94c, which, in turn, can capacitively coupled to an adjacent shield 94,94b,94c and travel to the lead tip. The gaps G also serve to prevent the picked up energy from traveling to the end of the lead and dissipating at the location where the lead electrode contacts the surrounding body tissue, which can cause a temperature rise in the body tissue at this location.

Figure 13:
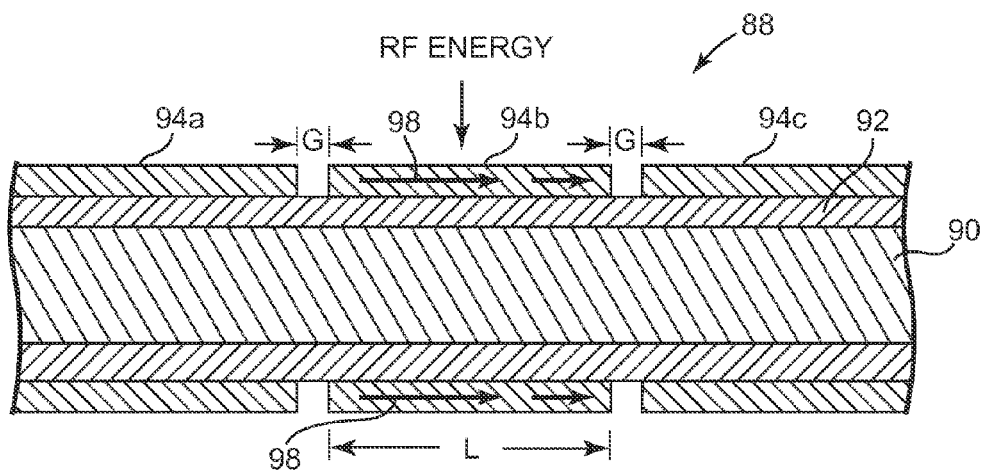
FIG. 13 is another longitudinal cross-sectional view of the lead of FIG. 12, showing the energy flow path of the RF electromagnetic energy received by the lead in the presence of an MRI field.

FIG. 13 is another longitudinal cross-sectional view of the lead 88 of FIG. 12, showing the energy flow path of the RF electromagnetic energy received by the lead 88 in the presence of an MRI field. As shown in FIG. 13, RF energy transmitted into the patient's body during an MRI scan is received on each of the outer restive shields 94a,94b,94c. Due to the relatively high resistance of the shields 94a,94b,94c, and as indicated generally by reference arrows 98, the RF energy is dissipated at or near the surface of the lead 88 along only the length L of each shield 94a,94b,94c. The small gap G between each of the shields 94a,94b,94c prevents the RF energy induced on one of the shields (e.g., shield 94b) from being transmitted to an adjacent shield (e.g., shield 94c). As a result, the flow of RF energy on one section of the lead 88 is interrupted and prevented from being transmitted along the entire length of the lead 88 to the lead tip. The interrupted RF energy is thus reflected back due to the mismatch in the impedance and is eventually dissipated within the resistive shield 94a,94b,94c.

Figure 14:
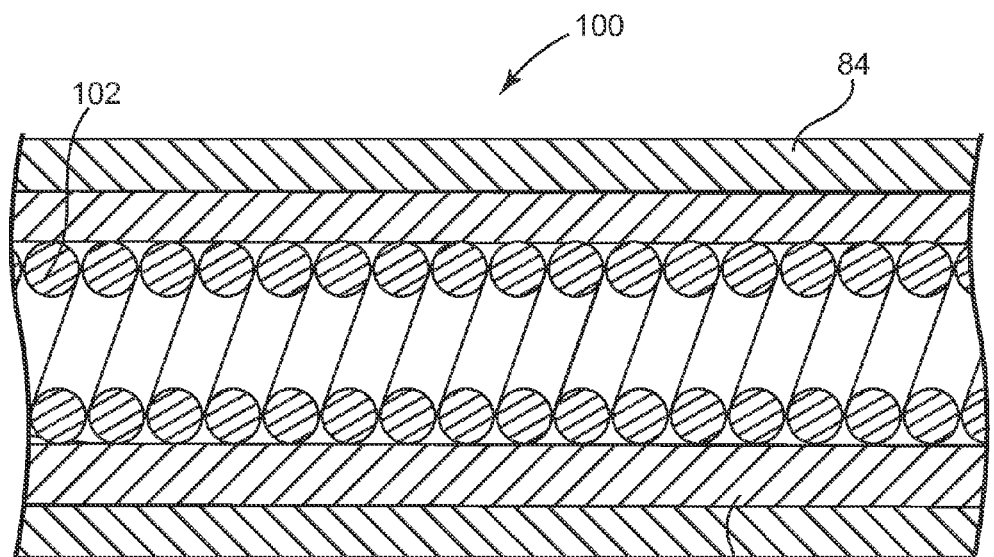
FIG. 14 is a longitudinal cross-sectional view showing a lead in accordance with another illustrative embodiment having a helically-shaped inner conductor coil surrounded by a resistive shield.

FIG. 14 is a longitudinal cross-sectional view showing a lead 100 in accordance with another illustrative embodiment having a helically-shaped inner conductor coil surrounded radially by a resistive shield. As shown in FIG. 14, the lead 100 is similar to the lead 80 described with respect to FIGS. 10-11, with like elements labeled in like fashion in the drawings. In the embodiment of FIG. 14, however, the inner conductor 102 is a helically-shaped conductor coil that extends through the interior of the lead 100, and which adds inductance to the lead 100 at MRI RF frequencies, thus increasing the impedance and inhibiting transmission of the RF energy along the length of the lead 100. In contrast to the outer resistive shield 84, the conductor coil 102 is fabricated from an electrically conductive, low resistance material configured to facilitate low-energy transmission of therapeutic energy to the electrodes on the lead 100. In some embodiments, for example, the inner conductor coil 102 is fabricated from a silver filled MP35N wire containing approximately 28% to 30% silver whereas the outer resistive member 84 comprises different, more resistive material.

Figure 15:
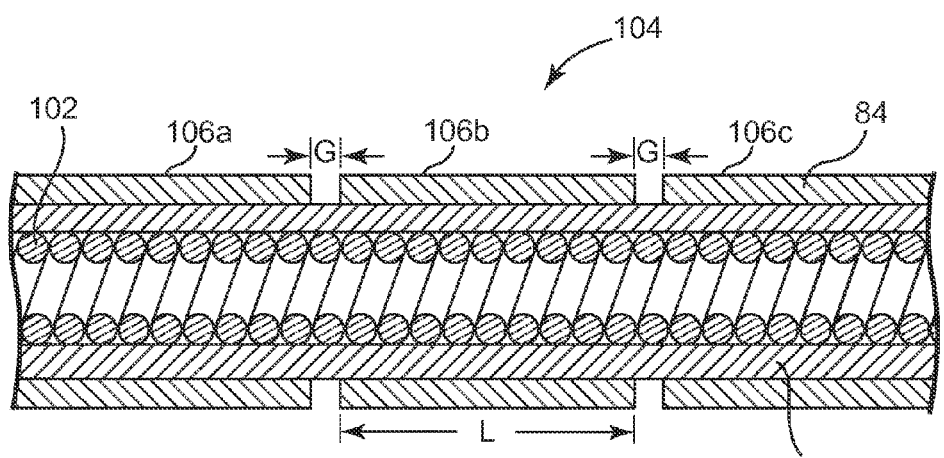
FIG. 15 is a longitudinal cross-sectional view showing a lead in accordance with another illustrative embodiment having a number of resistive shields spaced apart and electrically isolated from each other along the length of the lead.

In the embodiment of FIG. 14, the outer resistive shield 84 may extend continuously and uninterrupted along all or a portion of the length of the lead 100. In another illustrative lead 104 depicted in FIG. 15, the lead 104 includes a number of outer resistive shields 106a,106b,106c each spaced apart and electrically isolated from each other along the length of the lead 104 via a number of small gaps G, as shown. The length L of each of the outer resistive shields 106a,106b,106c can be selected to detune the lead 104 and prevent resonance based on the frequency of the RF energy provided by the MRI device. In some embodiments, for example, each of the outer resistive shields 106a,106b,106c has a length L that is less than or equal to ¼ of the wavelength of the RF energy received on the lead 104.

Figure 16:
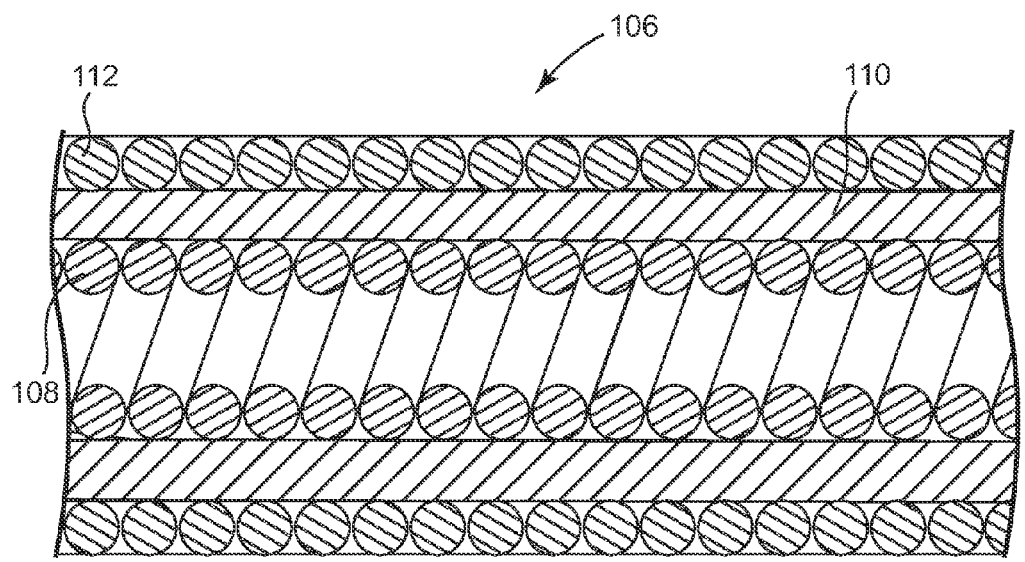
FIG. 16 is a longitudinal cross-sectional view showing a lead in accordance with another illustrative embodiment having a helically-shaped inner conductor coil surrounded by a helically-shaped resistive coil.

FIG. 16 is a longitudinal cross-sectional view showing a lead 106 in accordance with another illustrative embodiment having a helically-shaped inner conductor coil surrounded radially by a helically-shaped resistive coil. The lead 106 is similar to the lead 100 described with respect to FIG. 14, including a helically-shaped inner conductor coil 108 that can be used as an electrical conduit for supplying energy to one or more electrodes on the lead 106, a layer of insulation 110 radially surrounding the inner conductor coil 108, and an outer resistive shield 112 having a relatively high resistance compared to the resistance of the inner conductor coil 108 for dissipating absorbed RF energy along the length of the lead 106. In some embodiments, the inner conductor coil 108 is a single-filar wire coil. In other embodiments, the inner conductor coil 108 is a multi-filar wire coil.

In the embodiment of FIG. 16, the outer resistive shield 112 comprises a helically-shaped resistive coil that radially surrounds the inner conductor coil 108 and the layer of insulation 110. The resistive coil 112 has a relatively high resistance in comparison to the resistance of the inner conductor coil 108 to facilitate dissipation of RF energy received on the lead 106 into the surrounding body tissue along the length of the lead 106. In some embodiments, for example, the ratio of the resistance of the resistive coil 112 to the resistance of the inner conductor coil 108 may be in the range of between about 2 to 10. In one embodiment, the inner conductor coil 102 is fabricated from a silver filled MP35N wire containing approximately 28% to 30% silver whereas the outer resistive member 84 comprises different, more resistive material such as a pure MP35N.

Figure 17:
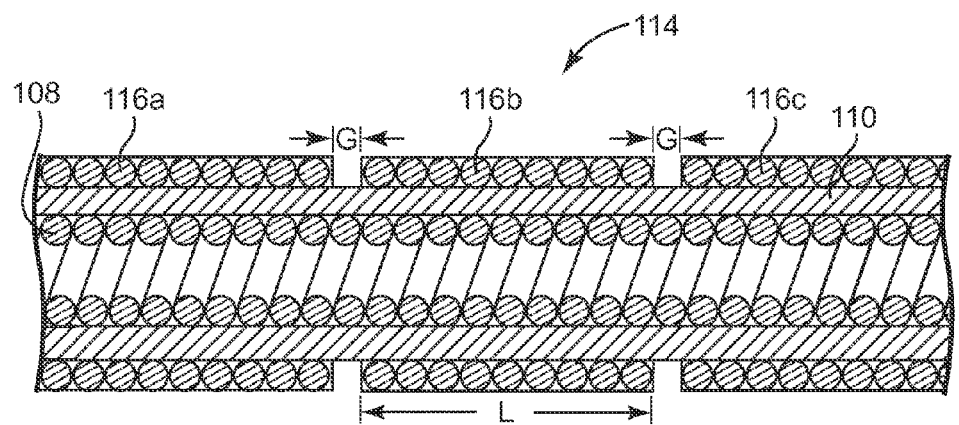
FIG. 17 is a longitudinal cross-sectional view showing a lead in accordance with another illustrative embodiment having a helically-shaped inner conductor coil and a number of helically-shaped resistive coils spaced apart and electrically isolated from each other along the length of the lead.

In the embodiment of FIG. 16, the resistive coil 112 may extend continuously and uninterrupted along all or a portion of the length of the lead 106. In another illustrative lead 114 depicted in FIG. 17, the lead 114 includes a number of resistive coils 116a,116b,116c each spaced apart and electrically isolated from each other along the length of the lead 114 via a number of small gaps G, as shown. The length L of each of the resistive coils 116a,116b,116c can be selected to detune the lead 114 and prevent resonance based on the frequency of the RF energy transmitted by the MRI device. In some embodiments, for example, each of the resistive coils 116a, 116b,116c has a length L that is less than or equal to ¼ of the wavelength of the RF energy received by the lead 114.

Figure 18:
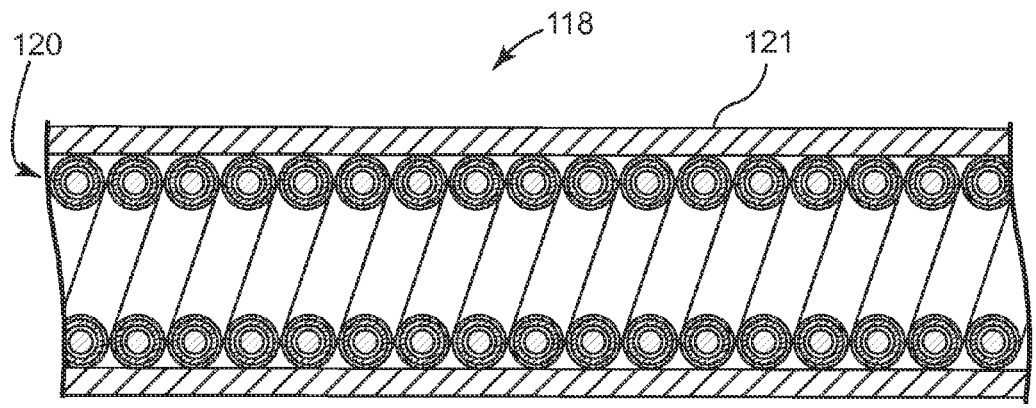
FIG. 18 is a longitudinal cross-sectional view showing a lead in accordance with another illustrative embodiment having a helically-shaped conductor coil with an integrated resistive shield.

FIG. 18 is a longitudinal cross-sectional view showing a lead 118 in accordance with another illustrative embodiment. As shown in FIG. 18, the lead 118 includes a helically-shaped conductor coil 120 that extends along at least a portion of the length of the lead 118. The conductor coil 120 is configured as an electrical conduit for supplying energy to the one or more electrodes on the lead 118. In certain embodiments, the conductor coil 120 is encased within an outer member 121 which serves to radially constrain the conductor coil 120 along the length of the lead 118. In some embodiments, for example, the outer member 121 comprises a jacket of silicone or polyurethane disposed radially about the conductor coil 120.

Figure 19:
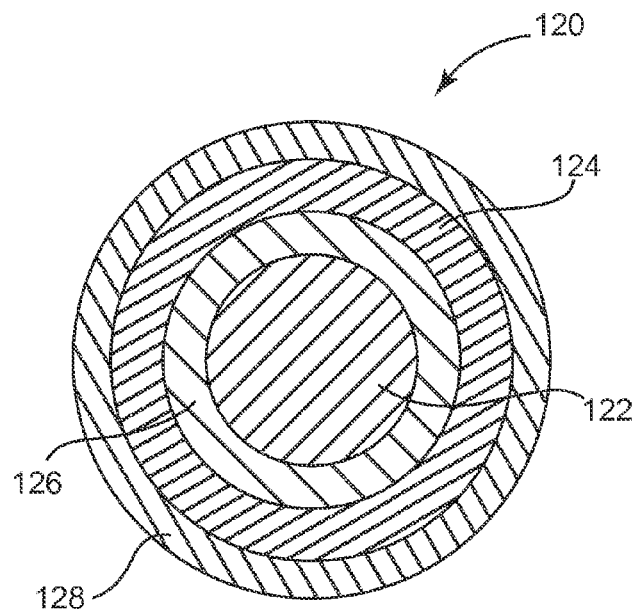
FIG. 19 is a transverse cross-sectional view showing the configuration of the helical conductor coil of FIG. 18 in greater detail.

FIG. 19 is a transverse cross-sectional view showing the configuration of the conductor coil 120 of FIG. 18 in greater detail. As further shown in FIG. 19, the conductor coil 120 includes an inner conductive core 122 and an outer resistive shield 124 radially disposed about the inner core 122. The resistive shield 124 can be formed integrally with the inner conductive core 122 (e.g., by a co-extrusion process), and comprises a material having a resistance that is greater than the resistance of the conductor core 122. In some embodiments, for example, the ratio of the resistance of the resistive shield 124 to the resistance to the conductor core 122 can be in the range of between about 2 to 10.

In the embodiment of FIGS. 18-19, the conductor coil 120 further includes a layer or coating of insulation 126 disposed between the inner conductor core 122 and the outer resistive shield 124. In some embodiments, a second layer or coating of insulation 128 may also be provided over the outer, resistive shield 124 to further insulate the shield 124.

Figure 20:
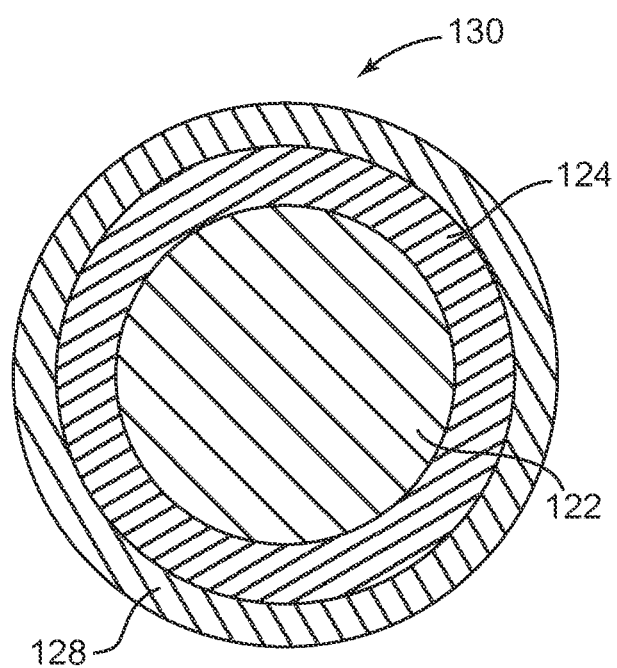
FIG. 20 is a transverse cross-sectional view showing another helically-shaped conductor coil with an integrated resistive shield.

If certain embodiments, and as further shown in FIG. 20, the first layer or coating of insulation 126 can be eliminated between the inner conductor core 122 and the outer resistive shield 124. If, for example, the skin depth of the resistive shield 124 is sufficiently large (e.g., greater than 4), than the first layer or coating of insulation 126 may be eliminated since the alternating currents produced by the RF energy are unable to penetrate sufficiently through the depth of the shield 124 due to the decline in current density at the interface between the shield 124 and the inner conductor core 122.

In those embodiments in which the conductor is coiled, the geometry of the coil conductor, including the outer diameter and pitch of the coil conductor, can be configured so as to increase the inductance and hence the impedance of the lead in order to inhibit the transfer of energy along the length of the lead. In some embodiments, for example, the inductance of the coil conductor can be increased by increasing the number of coil turns (e.g., by decreasing the pitch of the coil conductor), by increasing the outer diameter of the coil conductor, or by a combination of both. Since the impedance of a coil conductor is based in part on its inductance, increasing the inductance of the coil conductor by increasing the number of coil turns and/or increasing the outer diameter of the conductor results in an increase in the overall impedance of the conductor. Since the overall impedance of the lead at RF frequencies in MRI applications (e.g., 64 MHz) is partly a function of the inductance of the lead, this increase in the coil conductor inductance results in a decrease in the transfer of absorbed RF energy by the lead along its length towards the lead electrode.

In some embodiments, the coil conductor can comprise a helically-shaped wire coil conductor having a width of about 0.005 inches and a coil diameter (i.e., outer diameter) in the range of between about 0.016 inches to about 0.066 inches. In certain embodiments, for example, the coil conductor can have a coil diameter of at least 0.036 inches, 0.050 inches, 0.060 inches, or 0.066 inches. Other coil diameter configurations, however, are possible.

The pitch of the coil conductor can also be configured so as to increase the inductance and hence the impedance of the lead. In some embodiments the pitch of conductor can be in the range of between about 0.005 inches to 0.160 inches. Other coil pitch configurations, however, are possible. In general, as the coil pitch increases, the heating at the lead electrode also increases. For a 0.035 inch outer diameter coil, and in some embodiments, the pitch of the conductor should be no greater than about 0.008 inches, and more specifically, about 0.005 inches. For larger outer diameter coils, however, the minimum pitch can be larger, in some embodiments up to and including about 0.025 inches.

Figure 21:
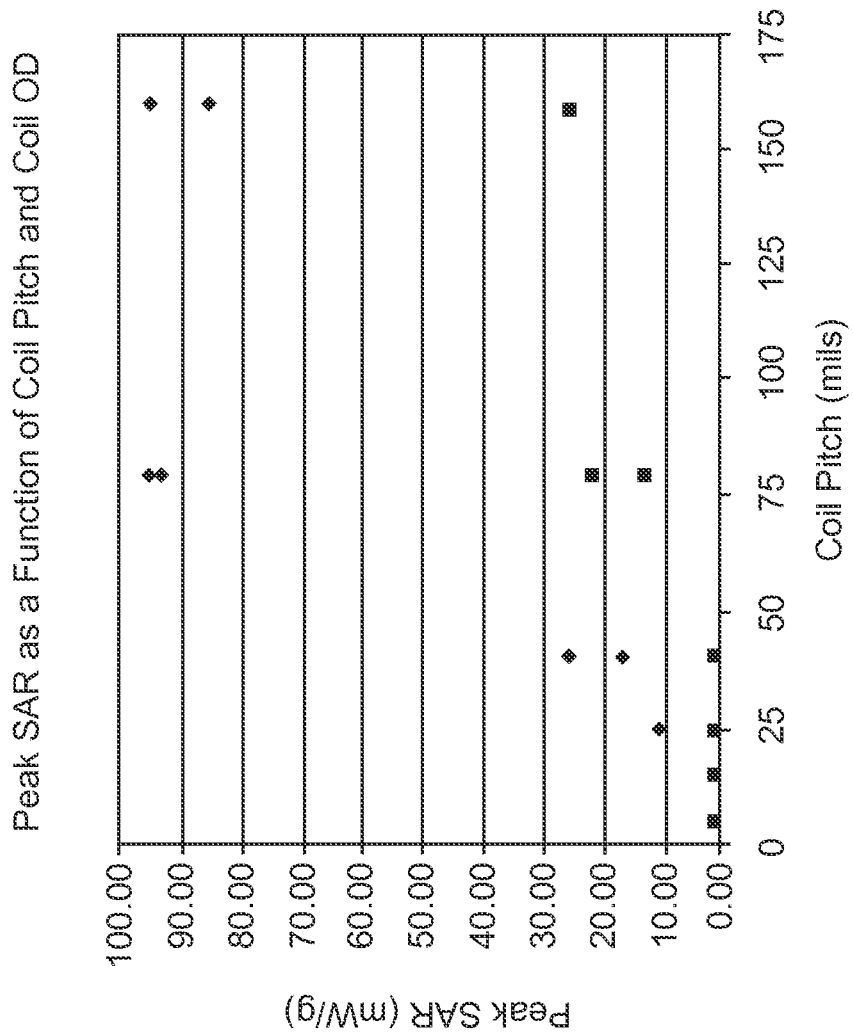
FIG. 21 is a chart showing the interdependence of coil pitch and coil diameter on the amount of RF energy absorbed by a helically-shaped wire coil conductor.

A strong interdependence exists between the coil pitch and the coil diameter of the coil conductor as the coil pitch increases and the coil diameter decreases. FIG. 21 is a chart showing the interdependence of coil pitch and coil diameter on the amount of absorbed RF energy transferred by a helically-shaped wire coil conductor to a distal lead tip. FIG. 21 may represent, for example, the peak specific absorption rate (SAR) as a function of coil pitch and coil diameter for a 0.036 inch coil diameter wire conductor and a 0.066 inch coil diameter wire conductor, each conductor having a length of about 50 cm and comprising an MP35N material. As the coil pitch of each of the conductors increases, the peak SAR, representing the amount of RF energy absorbed by the conductor, increases as a quadratic function. As shown in FIG. 21, a coil pitch greater than about 0.020 inches (20 mils) for a 0.036 inch wire coil, and a coil pitch greater than about 0.050 inches (50 mils) for a 0.066 inch wire coil, results in a significant rise in peak SAR that can increase the temperature of the body tissue at the lead electrode. As further shown in FIG. 21, at equivalent coil pitch values, the peak SAR for the larger coil diameter conductor is generally smaller than the peak SAR for the smaller coil diameter conductor.

Other design parameters of the lead can also be selected so as to reduce lead heating by the lead. In some embodiments, for example, the insulation provided about the coil conductor can be selected so as to reduce lead heating. The insulation thickness changes how much energy is coupled into or out of the surrounding body tissue along the length of the lead. In some cases, a relatively thin insulation, or insulations with higher dielectric constants, can minimize the temperature rise of a lead at the point of contact with the body tissue. An example of a relatively thin insulation for a coiled wire conductor has a wall thickness of less than about 0.015 inches, although other insulation thicknesses are possible.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical lead for use in a magnetic resonance imaging (MRI) environment, the lead comprising:
   a lead having a proximal portion, a distal portion having an electrode, and a conductor wire;
   the conductor wire having a center portion and an outer portion, the conductor wire having a resistivity that increases across a width of the conductor wire such that the resistivity of the conductor wire is greater at the outer portion than at the center portion; and
   wherein the increasing resistivity across the width of the conductor wire is configured to dissipate RF electromagnetic energy received along the lead and inhibit alternating current from being transmitted to the electrode.

2. The lead of claim 1, wherein the resistivity increases at a plurality of finite locations across the width of the conductor wire.

3. The lead of claim 1, wherein the conductor wire comprises a plurality of conductive layers.

4. The lead of claim 3, wherein the conductive layers successively increase in resistivity across the width of the conductor wire.

5. The lead of claim 3, wherein the plurality of conductive layers comprises a first outer conductor layer with a first resistivity, a second outer conductor layer with a second resistivity greater than the first resistivity, and a third outer conductor layer with third resistivity greater than the first and second resistivities.

6. The lead of claim 1, wherein the outer portion comprises a plurality of outer resistive shields that successively increase in resistivity.

7. The lead of claim 1, wherein the conductor wire is the only conductor wire that extends along the length of the lead.

8. The lead of claim 1, wherein the conductor wire continuously increases in resistivity from the center portion to the outer portion of the conductor wire.

9. The lead of claim 1, wherein an outer surface of the conductor wire defines an outer surface of the lead.

10. The lead of claim 1, wherein the resistivity increases gradually across the width of the conductor wire.

11. An implantable medical lead for use in a magnetic resonance imaging (MRI) environment, the lead comprising:
    a lead having a proximal portion, a distal portion having an electrode, and a conductor wire that extends from the proximal portion to the distal portion and electrically connects with the electrode;
    the conductor wire having a center portion and an outer portion, the conductor wire having a resistivity that changes across a width of the conductor wire such that the resistivity of the conductor wire is different between the outer portion and the center portion; and
    wherein the changing resistivity across the width of the conductor wire is configured to dissipate RF electromagnetic energy received along the lead and inhibit alternating current from being transmitted to the electrode.

12. The lead of claim 11, wherein the conductor wire comprises a plurality of conductive layers.

13. The lead of claim 12, wherein the conductive layers successively change in resistivity across the width of the conductor wire.

14. The lead of claim 12, wherein the plurality of conductive layers comprises a first outer conductor layer with a first resistivity, a second outer conductor layer with a second resistivity different than the first resistivity, and a third outer conductor layer with third resistivity different than the first and second resistivities.

15. The lead of claim 11, wherein the outer portion comprises a plurality of outer resistive shields that successively change in resistivity.

16. The lead of claim 11, wherein the conductor wire is the only conductor wire that extends along the length of the lead.

17. The lead of claim 11, wherein the conductor wire continuously changes in resistivity from the center portion to the outer portion of the conductor wire.

18. The lead of claim 11, wherein an outer surface of the conductor wire defines an outer surface of the lead.

19. The lead of claim 11, wherein the resistivity changes gradually across the width of the conductor wire.

20. The lead of claim 11, wherein the resistivity changes at a plurality of finite locations across the width of the conductor wire.

* * * * *